United States Patent [19]

Missbach

[11] Patent Number: 5,378,719

[45] Date of Patent: Jan. 3, 1995

[54] IMIDAZOLES

[75] Inventor: Martin Missbach, Rheinfelden, Switzerland

[73] Assignee: Ciba-Geigy Corporation, Ardsley, N.Y.

[21] Appl. No.: 196,880

[22] Filed: Feb. 15, 1994

Related U.S. Application Data

[63] Continuation of Ser. No. 990,220, Dec. 14, 1992.

[30] Foreign Application Priority Data

Dec. 18, 1991 [CH] Switzerland ............... 3751/91-8

[51] Int. Cl.$^6$ ............... C07D 417/12; A61K 31/425
[52] U.S. Cl. ............................. 514/369; 548/184
[58] Field of Search ...................... 548/184; 514/369

[56] References Cited

U.S. PATENT DOCUMENTS

| | | | |
|---|---|---|---|
| 3,699,116 | 10/1972 | Meisel | 548/184 |
| 4,697,020 | 9/1987 | Storni et al. | 548/184 |
| 5,137,897 | 8/1992 | Thorwart | 514/365 |

FOREIGN PATENT DOCUMENTS

| | | |
|---|---|---|
| 69154 | 1/1983 | European Pat. Off. . |
| 69784 | 1/1983 | European Pat. Off. . |
| 2632745 | 6/1975 | Germany . |
| 1325061 | 8/1973 | United Kingdom . |

OTHER PUBLICATIONS

March, Advanced Org. Chem. 3rd Ed. pp. 784–786 (1985).
Weisenberg, et al. "Suppression and augmentation of rat adjuvant arthritis with monoclonal anti-interferon–gamma antibody" Clin. Exp. Immunol. 78:245.
Vigorita, et al. "[3,3'-Bi-1,3-thiazolidine]-4,4'-dione system," Chemical Abstracts 102(11):18 No. 89678x (1985).
European Patent Office Search Mar. 12, 1993.

Primary Examiner—Robert Gerstl
Attorney, Agent, or Firm—Irving M. Fishman; Karen G. Kaiser

[57] ABSTRACT

Novel imidazoles of formula I

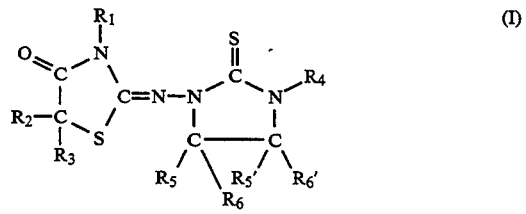

wherein
$R_1$ and $R_4$ are lower alkyl, lower alk-2-en-1-yl or lower alk-2-yn-1-yl,
$R_2$ and $R_3$ are each independently of the other hydrogen or lower alkyl or together form lower alkylidene, and
$R_5$ and $R_6$ are each hydrogen or lower alkyl or together form oxo, and
$R_5'$ and $R_6'$ have the same definitions as $R_5$ and $R_6$, with the proviso that at least one of the substituent pairs $R_5$ and $R_6$ or $R_5'$ and $R_6'$ together form oxo, and salts thereof, processes for the preparation of the said compounds, pharmaceutical compositions comprising them and the use thereof as medicinal active ingredients.

8 Claims, No Drawings

IMIDAZOLES

This is a continuation of Ser. No. 07/990,220, filed Dec. 14, 1992.

The invention relates to novel imidazoles of formula I

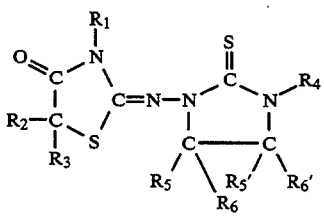

wherein $R_1$ and $R_4$ are lower alkyl, lower alk-2-en-1-yl or lower alk-2-yn-1-yl, $R_2$ and $R_3$ are each independently of the other hydrogen or lower alkyl or together form lower alkylidene, and $R_5$ and $R_6$ are each hydrogen or lower alkyl or together form oxo, and $R_5'$ and $R_6'$ have the same definitions as $R_5$ and $R_6$, with the proviso that at least one of the substituent pairs $R_5$ and $R_6$ or $R_5'$ and $R_6'$ together form oxo, and salts thereof, to processes for the preparation of the said compounds, to pharmaceutical compositions comprising them and to the use thereof as medicinal active ingredients.

Hereinbefore and hereinafter, lower radicals and compounds are to be understood as being, for example, those having up to and including 7, preferably up to and including 4, carbon atoms (C atoms).

Lower alk-2-en-1-yl is, for example, $C_3$–$C_5$alk-2-en-1-yl, such as, especially, allyl or methallyl.

Lower alk-2-yn-1-yl is, for example, $C_3$–$C_5$alk-2-yn-1-yl, such as, especially, prop-2-yn-1-yl or but-2-yn-1-yl.

Lower alkyl is, for example, $C_1$–$C_4$alkyl, such as methyl, ethyl, propyl or butyl.

Lower alkylidene is, for example, $C_1$–$C_4$alkylidene, such as, especially, methylene.

Pharmaceutically acceptable acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citrates. Salts of compounds of formula I are, for example, the acid addition salts thereof, for example the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

The compounds of formula I and the pharmaceutically acceptable salts thereof have valuable pharmacological properties. In particular, they exhibit marked anti-arthritic properties. Those properties can be demonstrated in vivo, for example, in the adjuvant arthritis model in rats in accordance with I. Wiesenberg et at., Clin. Exp. Immunol. 78, 245 (1989) in doses of approximately from 0.1 to 0.3 mg/kg and above p.o. or i.p.

The compounds of formula I and the pharmaceutically acceptable salts thereof can therefore be used in the treatment of diseases of the rheumatoid type. Those diseases include, especially, rheumatoid arthritis, juvenile arthritis, ankylosing spondylitis and other seronegative spondylarthritises, for example spondylarthritis in Colitis ulcerosa and Crohn's disease, and also reactive arthritises, collagen diseases, such as Lupus erythematosus, degenerative rheumatic diseases, extra-articular rheumatic and para-rheumatic diseases, for example gout and osteoporosis.

The invention relates especially to compounds of formula I wherein $R_1$ is $C_3$–$C_5$alk-2-en-1-yl or $C_3$–$C_5$alk-2-yn-1-yl and $R_4$ is $C_1$–$C_4$alkyl, $C_3$–$C_5$alk-2-en-1-yl or $C_3$–$C_5$alk-2-yn-1-yl, $R_2$ and $R_3$ are each independently of the other hydrogen or $C_1$–$C_4$alkyl or together form $C_1$–$C_4$alkylidene and $R_5$ and $R_6$, and $R_5'$ and $R_6'$ are each independently of the other hydrogen or $C_1$–$C_4$alkyl or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates more especially to compounds of formula I wherein the radical $R_1$ is $C_3$–$C_5$alk-2-en-1-yl, such as allyl or methallyl, or $C_3$–$C_5$alk-2-yn-1-yl, such as prop-2-yn-2-yl, and $R_4$ is $C_1$–$C_4$alkyl, such as methyl, or $C_3$–$C_5$alk-2-en-1-yl, such as allyl or methallyl, $R_2$ and $R_3$ are both hydrogen or the same $C_1$–$C_4$alkyl groups, such as methyl, or together form $C_1$–$C_4$ alkylidene, such as methylene, and $R_5$ and $R_6$, and $R_5'$ and $R_6'$ are each hydrogen or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates especially to compounds of formula I wherein $R_1$ is allyl or methallyl, $R_2$ and $R_3$ are both hydrogen or methyl, $R_4$ is methyl, allyl or methallyl and $R_5$ and $R_6$, and $R_5'$ and $R_6'$ are each hydrogen or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates specifically to the compounds of formula I mentioned in the Examples and salts thereof, especially pharmaceutically acceptable salts thereof.

Process a) for the preparation of the compounds provided according to the invention is carried out as follows: a compound of formula II

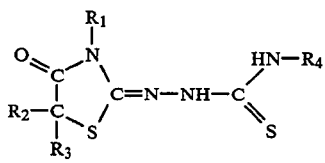

is condensed with a corresponding compound of formula III

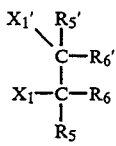

wherein $X_1$ and $X_1'$ are each reactive esterified hydroxy, and $R_5$, $R_6$, $R_5'$ and $R_6'$ are as defined above, in the presence of a basic condensation agent.

The condensation is effected in the presence of a basic condensation agent, such as a tertiary organic base, such as a tri-lower alkylamine, a Hünig base or an organic nitrogen base, such as pyridine or quinoline, and/or with cooling, advantageously in a temperature range of approximately from 25° to −70° C., for example from 0° to −60° C., especially from −40° to −60° C.

The compounds of formula II and processes for the preparation thereof, which are based on methods known per se, are known and are described, for example, in GB Patent 1 325 061, U.S. Pat. No. 4,697,020, DE Patent 2 405 395 or DE Patent 2 632 745 as intermediates for the preparation of tumour-inhibiting medicinal active ingredients.

In starting materials of formula III, removable radicals $X_1$ and $X_1'$ that come into consideration are, for example, reactively esterified hydroxy groups, especially halogen, such as chlorine or bromine. Compounds of formula III are known and are, for example, oxalyl chloride or haloacetyl halides, for example bromoacetyl chloride or bromide.

The condensation of compounds of formula II with compounds of formula III is effected in customary manner, advantageously in an inert solvent, for example an aliphatic halogenated hydrocarbon, such as in dichloromethane, or an aliphatic or cycloaliphatic ether, for example in tetrahydrofuran or dioxane. In a preferred form of process variant a), for example, a compound of formula II is reacted in the presence of triethylamine or pyridine and in dichloromethane or tetrahydrofuran as solvent with a compound of formula III, for example oxalyl chloride or a haloacetyl halide, for example bromoacetyl chloride or bromide, at a temperature of from −40° to −60° C.

In accordance with a further process variant b) it is possible to prepare compounds of formula I as follows: in compounds of formula IV

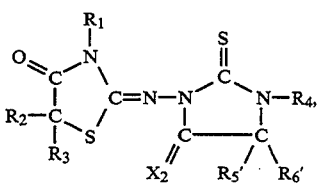

wherein $X_2$ is a functionally modified oxo group and $R_1$, $R_2$, $R_3$, $R_4$, $R_5'$ and $R_6'$ are as defined, or in corresponding salts thereof, the group $X_2$ is converted into oxo.

In starting materials of formula IV according to process variant b), functionally modified oxo is, for example, imino or hydroxy.

Starting materials of formula IV are prepared, for example, by reacting the corresponding compounds of formula II with cyanoformic acid or with one of its reactive derivatives, cyanoformyl chloride.

In accordance with a further process variant c), compounds of formula I can be prepared by reacting compounds of formula V

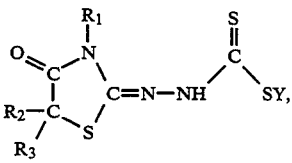

wherein $R_1$, $R_2$ and $R_3$ are as defined above and Y is lower alkyl, with compounds of formula VI

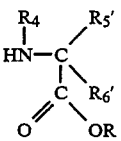

wherein $R_4$, $R_5'$ and $R_6'$ are as defined above and R is hydrogen or lower alkyl. The reaction of a compound of formula V with a compound of formula VI is effected in an inert solvent, such as lower alkanol, for example ethanol, and optionally in the presence of a basic condensation agent, such as a tertiary organic base, such as a tri-lower alkylamine, a Hünig base or an organic nitrogen base, such as pyridine or quinoline.

Starting compounds of formula V are novel and can be obtained from the corresponding hydrazone compound of formula VII

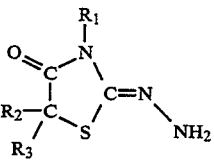

by reaction with carbon disulfide $CS_2$ and subsequent reaction with a lower alkyl iodide. The reaction of a compound of formula VII with carbon disulfide is effected in the presence of a tertiary organic base, such as a tri-lower alkylamine, a Hünig base or an organic nitrogen base, for example pyridine or quinoline. The subsequent reaction with a lower alkyl iodide in situ is effected with cooling of the resulting reaction mixture to a temperature of from $-10°$ to $+10°$ C., preferably to a temperature of from $0°$ to $+5°$ C.

Compounds of formula I in which $R_5$ and $R_6$ together form oxo and $R_5'$ and $R_6'$ are each hydrogen, or $R_5'$ and $R_6'$ together form oxo and $R_5$ and $R_6$ are each hydrogen, can also be prepared in accordance with a further process variant d) by reacting a compound of formula VIII $$\text{(VIII)} \quad \underset{R_1}{\text{HN}}\diagdown\underset{\underset{S}{\overset{\|}{C}}}{C}\diagup\overset{NH}{}\diagdown\underset{\underset{R_6}{\overset{R_5}{|}}\underset{R_5'}{\overset{R_6'}{|}}}{N}\underset{C-C}{\overset{\overset{S}{\overset{\|}{C}}}{}}\diagdown N-R_4,$$

wherein $R_1$, $R_4$, $R_5$, $R_6$, $R_5'$ and $R_6'$ are as defined above, with a compound of formula IX $$\text{(IX)} \quad \underset{R_2}{\overset{Y-C}{|}}\underset{R_3}{\overset{|}{C}}\diagdown\underset{OR}{\overset{O}{C}\diagup\kern-0.5em\diagdown}$$

wherein $R_2$ and $R_3$ are as defined above, Y is reactive esterified hydroxy and R is hydrogen or lower alkyl. The reaction of a compound of formula VIII with a compound of formula IX is effected in an inert solvent, such as a lower alkanol, for example ethanol, and optionally in the presence of a basic condensation agent, such as a tertiary organic base, such as a tri-lower alkylamine, for example triethylamine, a Hünig base or an organic nitrogen base, such as pyridine, dimethylaminopyridine or quinoline. The reaction is advantageously effected in a temperature range of approximately $0°–80°$ C., for example $20°–80°$ C., especially $50°–80°$ C.

Starting materials of formula VIII are obtained by reacting compounds of formula X $$\text{(X)} \quad \underset{\underset{R_5}{\overset{\text{HN}}{\diagdown}}\underset{\underset{R_6}{\overset{|}{}}\underset{R_5'}{\overset{R_6'}{|}}}{H_2N}}{\overset{\overset{S}{\overset{\|}{C}}}{\diagdown}}\underset{C-C}{\overset{}{}}\diagdown N-R_4,$$

wherein $R_4$, $R_5$, $R_6$, $R_5'$ and $R_6'$ are as defined for formula VIII, with an isothiocyanate compound of formula XI $$R_1-NCS \quad \text{(XI)}.$$

The condensation of compounds of formula X with compounds of formula XI is effected in customary manner in an inert solvent, such as a lower alkanol, for example ethanol, in a temperature range of $0°–70°$ C., for example $20°–70°$ C., advantageously $50°–70°$ C.

In starting materials of formula IX, a suitable removable radical Y is, for example, a reactively esterified hydroxy group, especially halogen, such as chlorine or bromine. Compounds of formula IX are known and are also commercially available.

Compounds of formula X can be obtained, for example, by ring-closure of corresponding compounds of formula XII $$\text{(XII)} \quad H_2N-\underset{\underset{R_5}{\overset{|}{}}\underset{R_6}{\overset{|}{}}}{\overset{\overset{S}{\overset{\|}{C}}}{N}}\underset{C-C}{\overset{}{}}\diagdown\underset{X}{\overset{NH-R_4}{\diagup}}\diagdown\underset{}{\overset{O}{}}$$

wherein $R_4$, $R_5$ and $R_6$ are as defined above.

The condensation is effected in the presence of a basic condensation agent, such as a tertiary organic base, such as a tri-lower alkylamine, a Hünig base or an organic nitrogen base, such as quinoline, pyridine or especially dimethylaminopyridine, advantageously in a temperature range of from $20°$ C. to the reflux temperature of the inert solvent, especially from $50°$ C. to the reflux temperature of the inert solvent used. The inert solvent used is advantageously a lower alkanol, especially ethanol.

Compounds of formula XII can be obtained from corresponding hydrazinoacetic acid esters, especially the ethyl ester, by condensation with an isothiocyanate of formula XIII $$R_4-CNS \quad \text{(XIII)}$$

wherein $R_4$ is as defined above.

The condensation is effected in a manner analogous to that of compounds of formula X with compounds of formula XI.

The compounds of formula I obtainable by process variants a) to d) according to the invention in the form of an isomeric mixture may, if desired, be separated into the individual isomers, and/or free compounds obtainable in accordance with the invention may be converted into a salt, or a salt obtainable in accordance with the invention may be converted into a free compound or into a different salt.

Compounds obtainable in accordance with the process may be converted in customary manner into different compounds of formula I.

Resulting salts can be converted into the free compounds in a manner known per se, for example by treatment with a base, such as an alkali metal hydroxide, a metal carbonate or hydrogen carbonate, or ammonia, or with another salt-forming base mentioned at the beginning, or with an acid, such as a mineral acid, for example with hydrochloric acid, or with another salt-forming acid mentioned at the beginning.

Resulting salts can be converted into different salts in a manner known per se; for example acid addition salts can be converted by treatment with a suitable metal salt, such as a sodium, barium or silver salt, of a different acid in a suitable solvent in which an inorganic salt being formed is insoluble and is therefore eliminated from the reaction equilibrium, and basic salts can be converted by liberation of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinbefore and hereinafter any reference to the free compounds and their salts is to be understood as also including the corresponding salts and free compounds, respectively, where appropriate and expedient.

Resulting racemates can also be resolved into the optical antipodes according to known methods, for example by recrystallisation from an optically active solvent, with the aid of microorganisms or by reaction of the resulting diastereoisomeric mixture or racemate with an optically active auxiliary compound, for example in accordance with the acidic, basic or functionally modifiable groups present in compounds of formula I, with an optically active acid, base or an optically active alcohol, to form mixtures of diastereoisomeric salts or functional derivatives, such as esters, and separation thereof into the diastereoisomers from which the desired enantiomer can be freed in the appropriate customary manner. Bases, acids and alcohols suitable for this purpose are, for example, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluoyltartaric acid, D- or L-malic acid, D- or L-mandelic acid, or D- or L-camphorsulfonic acid, or optically active alcohols, such as borneol or D- or L-(1-phenyl)ethanol.

The invention relates also to those forms of the process according to which a compound obtainable as intermediate at any stage of the process is used as starting material and the remaining steps are carried out, or a starting material is used in the form of a salt or, especially, is formed under the reaction conditions.

The invention relates also to the novel starting materials that have been developed specifically for the preparation of the compounds according to the invention, especially the group of starting materials that result in the compounds of formula I that are described at the beginning as being preferred, to the processes for their preparation and to their use as intermediates.

The pharmaceutical compositions according to the invention, which comprise the compound according to the invention or a pharmaceutically acceptable salt thereof, are for enteral, such as oral and also rectal, and for parenteral administration to (a) warm-blooded animal(s), the compositions comprising the pharmacological active ingredient on its own or together with a pharmaceutically acceptable carrier. The daily dose of the active ingredient depends upon age and individual condition, and also upon the mode of administration.

The novel pharmaceutical compositions comprise, for example, from approximately 10% to approximately 80% active ingredient, preferably from approximately 20% to approximately 60% active ingredient. Pharmaceutical compositions according to the invention for enteral or parenteral administration are, for example, those in unit dose forms, such as dragées, tablets, capsules or suppositories, and also ampoules. Those compositions are prepared in a manner known per se, for example by means of conventional mixing, granulating, confectioning, dissolving or lyophilising processes. For example, pharmaceutical compositions for oral use can be obtained by combining the active ingredient with solid carriers, optionally granulating a resulting mixture, and, if desired, processing the mixture or granules, if necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical compositions include dry-filled capsules consisting of gelatin, and also soft, sealed capsules consisting of gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycol, to which stabilisers may likewise be added.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycol or higher alkanols. It is also possible to use gelatin rectal capsules that comprise a combination of the active ingredient with a base material. Suitable base materials are, for example, liquid triglycerides, polyethylene glycol or paraffin hydrocarbons.

For parenteral administration there are especially suitable aqueous solutions of an active ingredient in water-soluble form, for example in the form of a water-soluble salt, and also, suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, if desired, stabilisers.

The invention relates also to the use of the compounds of formula I, preferably in the form of pharmaceutical compositions. The dose of the active ingredient depends upon the species of warm-blooded animal, its age and individual condition and upon the mode of administration. In normal cases, the approximate daily dose for oral administration to a patient weighing about 75 kg is estimated to be from approximately 5 mg to approximately 1000 mg, especially from approximately 10 mg to approximately 200 mg. That dose can be administered all at once or can be divided into several, for example from 2 to 4, individual doses. Pharmaceutical compositions in unit dose form therefore comprise from approximately 5 mg to approximately 250 mg, especially from approximately 10 mg to approximately 50 mg, active ingredient.

The following Examples serve to illustrate the invention. Temperatures am given in degrees Celsius, pressures in mbar.

EXAMPLE 1

With stirring at from −55° to −60°, 2.5 ml of oxalyl chloride are added dropwise in the course of 5 minutes to a mixture of 6 g of 3-alyl-thiazolidine-2,4-dione-2-(4-methyl-3-thiosemicarbazone) and 7.5 ml of triethylamine in 200 ml of absolute methylene chloride and the mixture is then stirred at the same temperature for a further 30 minutes. The mixture is allowed to rise to 0° and then stirred at the same temperature for 15 minutes. The orange solution is extracted twice with ice-water and once with dilute sodium hydrogen carbonate solution and dried over sodium sulfate. The solvent is removed and the oil that remains behind is crystallised from 50 ml of ethanol, yielding 4.6 g of slightly orange crystals having a melting point of 126°–127°. Recrystallisation from ethanol containing a few drops of methylene chloride yields the analytically pure compound 1-(3-alyl-4-oxo-thiazolidin-2-ylidene)- 1-amino-3-methylimidazolidine-2-thione-4,5-dione. Melting point 128°
$^1$H-NMR: 3.45 (s, 3H), 3.95 (s, 2H), 4.5 (d, 2H), 5.25–5.4 (m, 2H), 5.9 (m, 1H).

EXAMPLE 2

In a manner analogous to Example 1, starting from 6.2 g of 3-methallyl-5,5-dimethyl-thiazolidine-2,4-dione-2-(4-allyl-3-thiosemicarbazone) and 2.7 g of oxalyl chloride them is obtained, after recrystallisation from ethanol, 1-(3-methallyl-5,5-dimethyl-4-oxo-thiazolidin-2oylidene)- 1-amino-3-allyl-imidazolidine-2-thione-4,5-dione. Melting point: 144°–145°;
$^1$H-NMR: 1.65 (s, 6H), 1.8 (s, 3H), 4.4 (s, 2H), 4.55 (d, 2H), 4.85 (s, 1H), 4.95 (s, 1H), 5.3 (m, 2H), 5.75–5.9 (m, 1H).

EXAMPLE 3

In a manner analogous to Example 1, starting from 2.5 g of 3-methallyl-5,5-dimethyl-thiazolidine-2,4-dione-2-(4-methyl-3-thiosemicarbazone) and 1.1 g of oxalyl chloride there is obtained, after recrystallisation from ethanol, 1-(3-methallyl-5,5-dimethyl-4-oxo-thiazolidin-2-ylidene)- 1-amino-3-methyl-imidazolidine-2-thione-4,5-dione. Melting point: 155°–156°;
$^1$H-NMR: 1.7 (s, 6H), 1.8 (s, 3H), 3.45 (s, 3H), 3.45 (s, 3H), 4.45 (s, 2H), 4.85 (s, 1H), 4.95 (s, 1H).

EXAMPLE 4

In a manner analogous to Example 1, starting from 4.9 g of 3-methyl-thiazolidine-2,4-dione-2-(4-allyl-3-thiosemicarbazone) and 1.9 g of oxalyl chloride there is obtained, after recrystallisation from ethanol, 1 -(3-methyl-4-oxo-thiazolidin-2-ylidene)- 1-amino-3-allyl-imidazolidine-2-thione-4,5-dione. Melting point: 152°–154°;
$^1$H-NMR: 3.35 (s, 3H), 3.9 (s, 2H), 4.5 (d, 2H), 5.25–5.35 (m, 2H), 5.8–5.95 (m, 1H).

EXAMPLE 5

In a manner analogous to Example 1, starting from 2 g of 3-allyl-thiazolidine-2,4-dione-2-(4-allyl-3-thiosemicarbazone) and 0.75 ml of oxalyl chloride there is obtained, after recrystallisation from ethanol, 1-(3-allyl-4-oxo-thiazolidin-2-ylidene)-1-amino-3-allyl-imidazolidine-2-thione-4,5-dione. Melting point: 138°;
$^1$H-NMR: 3.95 (s, 2H), 4.45 (d, 2H), 4.6 (d, 2H), 5.25–5.4 (m, 4H), 5.8–6.0 (m, 2H).

EXAMPLE 6

In a manner analogous to Example 1, starting from 2 g of 3-propyl-thiazolidine-2,4-dione-2-(4-methyl-3-thiosemicarbazone) and 1.14 g of oxalyl chloride there is obtained, after recrystallisation from ethanol, 1-(3-propyl-4-oxo-thiazolidin-2-ylidene)- 1-amino-3-methyl-imidazolidine-2-thione-4,5-dione. Melting point: 112°–113°;
$^1$H-NMR: 0.95 (t, 3H), 1.8 (dxq, 2H), 3.45 (s, 3H), 3.85 (t, 2H), 3.9 (s, 2H).

EXMAPLE 7

In a manner analogous to Example 1, starting from 1 g of 3-propynyl-thiazolidine-2,4-dione-2-(4-methyl-3-thiosemicarbazone) and 0.55 g of oxalyl chloride there is obtained, after recrystallisation from ethanol, 1-(3-propynyl-4-oxo-thiazolidin-2-ylidene)-1-amino-3-methyl-imidazolidine-2-thione-4,5-dione. Melting point: 173°–174°;
$^1$H-NMR: 2.3 (br, s, 1H), 3.4 (s, 3H), 3.95 (s, 2H), 4.6 (br, s, 2H).

EXAMPLE 8

With stirring at −60°, 2.7 ml of 2-bromoisobutyric acid bromide are added dropwise over a period of 5 minutes to a mixture of 4.9 g of 3-allyl-thiazolidine-2,4-dione-2-(4-methyl-3-thiosemicarbazone) and 6.2 ml of triethylamine in 100 ml of absolute methylene chloride and the mixture is stirred at the same temperature for 30 minutes. The suspension is allowed to rise to room temperature and the mixture is partitioned between water and methylene chloride. The aqueous phase is extracted a second time and the combined organic phases are dried over sodium sulfate and concentrated. Crystallisation from cold ethanol yields colourless crystals of a secondary product having an azine structure; the crystals are separated off and the mother liquor is concentrated and taken up in 30 ml of chloroform; 5 ml of triethylamine are added and the mixture is boiled at reflux for 2 hours. After cooling to room temperature, the mixture is partitioned between water and chloroform and the organic phase is dried over magnesium sulfate and then concentrated. Crystallisation from ethanol yields crystals which, after recrystallisation from methylene chloride/diethyl ether, yield the pure compound 1-(3-allyl-4-oxo-thiazolidin-2-ylidene)- 1-amino-3-methyl-5,5-dimethyl-imidazolidine-2-thion-4-one. Melting point: 142°;
$^1$H-NMR: 3.3 (s, 3H), 3.9 (s, 2H), 4.5 (d, 2H), 5.25–5.4 (m, 2H), 5.9 (m, 1H).

EXAMPLE 9 a) 1 g of a compound of formula VIII wherein $R_1$ is allyl and Y is methyl, and 0.4 g of sarcosine are boiled at reflux for 3.5 hours in 15 ml of ethanol and 0.4 g of triethylamine. The solvent is removed, the residue is taken up in methylene chloride and washed with 0.1N hydrochloric acid and water. After drying over magnesium sulfate and removal of the solvent there remains a yellowish oil from which the pure compound, 1-(3-allyl-4-oxo-thiazolidin-2-ylidene)-1-amino-3-methyl-imidazolidine-2-thion-5-one, is obtained in crystalline form from ethanol/methylene chloride. Melting point: 131°–133°;

1H-NMR: 3.3 (s, 3H), 3.9 (s, 2H), 4.5 (d, 2H), 5.25–5.4 (m, 2H), 5.9 (m, 1H).

b) The intermediate of formula VIII wherein $R_1$ is allyl and Y is methyl is obtained as follows:

10 g of 3-allyl-2,4-thiazolidinedione-2-hydrazone are dissolved in 100 ml of tetrahydrofuran; 8.2 ml of triethylamine and 3.6 ml of carbon disulfide are added and the mixture is stirred for 3 hours at room temperature. The mixture is cooled to −5° and then 4 ml of methyl iodide are added dropwise and the mixture is allowed to rise to room temperature and stirred for 2 hours. Water is then added to the mixture and the precipitated product is filtered off. The solid is dissolved in methylene chloride and dried over magnesium sulfate. After removal of ⅔ of the total volume of solvent, the product which has crystallised out is filtered off and dried in the air. Further product can be obtained from the mother liquor after chromatography on silica gel with methylene chloride. Melting point: 148–150°;

1H-NMR: 2.6 (s, 3H), 4.0 (s, 2H), 4.4 (d, 2H), 5.25–5.45 (m, 2H), 5.9 (m, 1H), 8.3 (br. s, 1H).

EXAMPLE 10

In a manner analogous to Example 9, 2.0 g of a compound of formula V wherein $R_1$ is allyl and $R_2$, $R_3$ and Y are methyl, and 1.23 g of sarcosine ethyl ester in 25 ml of ethanol are boiled at reflux for 6 hours with a spatula tip of dimethylaminopyridine. The mixture is cooled to 0° C. and the product crystallises out overnight at that temperature; the product is filtered off and washed with a small amount of ether and then dried, yielding, if desired after recrystallisation from methylene chloride/ether, the pure compound 1-(3-allyl-5,5-dimethyl-4-oxo-thiazolidin-2-ylidene)-1-amino-3-methyl-imidazolidine-2-thion-5-one. Melting point: 132°–133° C.

EXAMPLE 11

In a manner analogous to Example 9, 3.5 g of a compound of formula V wherein $R_1$ is allyl and Y is methyl, and 1.23 g of alanine methyl ester hydrochloride in 30 ml of ethanol are boiled for 8 hours at reflux with 2.1 ml of triethylamine and a spatula tip of dimethylaminopyridine. The mixture is concentrated and the residue is taken up in methylene chloride. The mixture is washed with dilute hydrochloric acid solution and then with dilute bicarbonate solution, dried over sodium sulfate and the solvent is removed in a rotary evaporator. Chromatography on silica gel yields the cyclised product together with the open-chain thiosemicarbazone as secondary product. The oily compound solidifies under a high vacuum to form a glassy foam of 1-(3-allyl-4-oxo-thiazolidin-2-ylidene)-1-amino-4-methyl-imidazolidine-2-thion-5-one. 1H-NMR: 1.55 (d, 3H), 3.9 (s, 2H), 4.25 (q, 1H), 4.5 (d, 2H), 5.3 (m, 2H), 5.8 (m, 1H), 7.85 (br.s, 1H).

EXAMPLE 12

7.5 g of bromoacetic acid are added to 12 g of 1-(3-methyl-4-oxo-2-thioxo-imidazolidin-1-yl)-3-allyl-thiourea and 9 g of anhydrous sodium acetate in 200 ml of ethanol and the mixture is stirred at 60° C. for 6 hours. The solvent is removed and the residue is partitioned between water and methylene chloride. The organic phase is dried with sodium sulfate and, after filtration, 150 ml of ethanol are added. The methylene chloride is removed in a rotary evaporator, the product crystallising. The mixture is cooled to 0° C. and the product is filtered off, washed with ether and dried, yielding, if desired after recrystallisation from methylene chloride/ether, the pure compound 1-(3-allyl-4-oxo-thiazolidin-2-ylidene)- 1 -amino-3-methyl-imidazolidine-2-thion-4-one having a melting point of 136°–137° C.

EXAMPLE 13

3.8 g of 2-bromoisobutyric acid are added to 4.8 g of 1-(3-methyl-4-oxo-2-thioxo-imidazolidin-1-yl)-3-allyl-thiourea and 4 g of anhydrous sodium acetate in 50 ml of ethanol and the mixture is stirred at 50° C. for 15 hours. The solvent is removed and the residue is partitioned between water and methylene chloride. The organic phase is dried with sodium sulfate and concentrated. The mixture is chromatographed on silica gel with methylene chloride and the product is then crystallised from methylene chloride/ether, yielding the pure compound 1-(3-allyl-5,5-dimethyl-4-oxo-thiazolidin-2-ylidene)-1-amino-3-methyl-imidazolidine-2-thion-4-one, melting point 121°–122° C.

EXAMPLE 14

Tablets, each comprising 10 mg of 1-(3-allyl-4-oxo-thiazolidin-2-ylidene)-1-amino-3-methyl-imidazolidine-2-thione-4,5-dione or a salt thereof, can be prepared as follows:

Composition ( 10 000 Tablets)

| active ingredient | 100.0 g |
| --- | --- |
| lactose | 450.0 g |
| potato starch | 350.0 g |
| gelatin | 10.0 g |
| talc | 60.0 g |
| magnesium stearate | 10.0 g |
| silicon dioxide (highly disperse) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 100.0 mg and comprising 50.0 mg of active ingredient; if desired the tablets may be provided with dividing notches for finer adaptation of the dose.

EXAMPLE 15

Hard gelatin capsules, each comprising 20 mg of active ingredient, 1-(3-allyl-4-oxo-thiazolidin-2-ylidene)- 1-amino-3-methyl-imidazolidine-2-thione-4,5-dione or a salt thereof, can be prepared, for example, as follows:

Composition (for 1000 Capsules)

| active ingredient | 20.0 g |
| --- | --- |
| lactose | 240.0 g |

-continued

| | |
|---|---|
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intemately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 300 mg portions of the resulting formulation are introduced into size 0 hard gelatin capsules.

EXAMPLE 16

Hard gelatin capsules, each comprising 100 mg of active ingredient, for example 1-(3-allyl-4-oxo-thiazolidin-2-ylidene)- 1-amino-3-methyl-imidazolidine-2-thione-4,5-dione or a salt thereof, can be prepared, for example, as follows:

Composition (for 1000 Capsules)

| | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 390 mg portions of the resulting formulation are introduced into size 0 hard gelatin capsules.

EXAMPLE 17

Film-coated tablets, each comprising 50 mg of 1-(3-allyl-4-oxo-thiazolidin-2-ylidene)-1-amino-3-methyl-imidazolidine-2-thione-4,5-dione or a salt thereof, can be prepared as follows:

Composition (for 1000 Film-Coated Tablets)

| | |
|---|---|
| active ingredient | 50.0 g |
| lactose | 100.0 g |
| corn starch | 70.0 g |
| talc | 10.0 g |
| calcium stearate | 2.0 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed together and moistened with a paste prepared from 15 g of corn starch and water (with heating), and granulated. The granules are dried and the remainder of the corn starch, the talc and the calcium stearate are added and mixed with the granules. The mixture is compressed to form tablets (weight: 240 mg) which are then film-coated with a solution of the hydroxy-propylmethylcellulose and the shellac in methylene chloride; final weight of the film-coated tablet: 283 mg.

EXAMPLE 18

A 0.2 % injection or infusion solution of 1-(3-allyl-4-oxo-thiazolidin-2-ylidene)-1-amino-3-methyl-imidazolidine-2-thione-4,5-dione, or a salt thereof, can be prepared, for example, as follows:

Composition (for 1000 Ampoules)

| | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the mixture is made up to 2500 ml with water. For the preparation of unit dose forms, 1.0 ml or 2.5 ml portions are introduced into glass ampoules which then comprise 2.0 mg or 5.0 mg of active ingredient, respectively.

EXAMPLE 19

A 1% ointment (O/W emulsion) comprising as active ingredient, for example, 1-( 3-allyl-4-oxo-thiazolidin-2-ylidene )- 1-amino-3-methyl-imidazolidine-2-thione-4,5-dione or a salt thereof, and having the following composition:

| | |
|---|---|
| active ingredient | 1.0 g |
| cetyl alcohol | 3.0 g |
| glycerol | 6.0 g |
| methylparaben | 0.18 g |
| propylparaben | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water q.s. ad | 100.0 g |

EXAMPLE 20

A 1% gel, comprising as active ingredient, for example, 1-(3-allyl-4-oxo-thiazolidin-2-ylidene)-1-amino-3-methyl-imidazolidine-2-thione-4,5-dione or a salt thereof, and having the following composition:

| | |
|---|---|
| active ingredient | 1.0 g |
| Carbopol 934 P | 1.0 g |
| glycerol | 3.0 g |
| isopropanol | 25.0 g |
| Softigen ® 767 | 0.2 g |
| demin. water q.s. ad | 100.0 g |

EXAMPLE 21

In a manner analogous to that described in the preceding Examples 14 to 20, it is also possible to prepare pharmaceutical compositions comprising a different compound of formula I or a phannaceutically acceptable salt thereof.

What is claimed is:

1. A compound of formula I

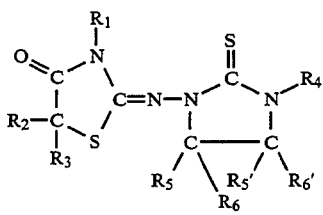

wherein

R$_1$ and R$_4$ are lower alkyl, lower alk-2-en-1-yl or lower alk-2-yn-1-yl,

R$_2$ and R$_3$ are each independently of the other hydrogen or lower alkyl or together form lower alkylidene, and R$_5$ and R$_6$ are each hydrogen or lower alkyl or together form oxo, and R$_5'$ and R$_6'$ have the same definitions as R$_5$ and R$_6$, with the proviso that at least one of the substituent pairs R$_5$ and R$_6$ or R$_5'$ and R$_6'$ together form oxo, or a salt thereof.

2. A compound according to claim 1 of formula I, wherein

R$_1$ is C$_3$–C$_5$alk-2-en-1-yl or C$_3$–C$_5$alk-2-yn-1-yl and

R$_4$ is C$_1$–C$_4$alkyl, C$_3$–C$_5$alk-2-en-1-yl or C$_3$–C$_5$alk-2-yn-1-yl, R$_2$ and R$_3$ are each independently of the other hydrogen or C$_1$–C$_4$alkyl or together form C$_1$–C$_4$alkylidene and R$_5$ and R$_6$, and R$_5'$ and R$_6'$ are each independently of the other hydrogen or C$_1$–C$_4$alkyl or together form oxo, with the proviso that at least one of the substituent pairs R$_5$ and R$_6$ or R$_5'$ and R$_6'$ together form oxo, or a salt thereof.

3. A compound according to claim 1 of formula I wherein the radical R$_1$ is C$_3$–C$_5$alk-2-en-1-yl, or C$_3$–C$_5$alk-2-yn-1-yl, and R$_4$ is C$_1$–C$_4$alkyl, or C$_3$–C$_5$alk-2-en-1-yl, R$_2$ and R$_3$ are both hydrogen or the same C$_1$–C$_4$alkyl groups, or together form C$_1$–C$_4$alkylidene, and R$_5$ and R$_6$, and R$_5'$ R$_6'$ are each hydrogen or together form oxo, with the proviso that at least one of the substituent pairs R$_5$ and R$_6$ or R$_5'$ and R$_6'$ together form oxo, or a pharmaceutically acceptable salt thereof.

4. A compound according to claim 1 of formula I wherein

R$_1$ is allyl or methallyl,

R$_2$ and R$_3$ are both hydrogen or methyl,

R$_4$ is methyl, allyl or methallyl and

R$_5$ and R$_6$, and R$_5'$ and R$_6'$ are each hydrogen or together form oxo, with the proviso that at least one of the substituent pairs R$_5$ and R$_6$ or R$_5'$ and R$_6'$ together form oxo, or a pharmaceutically acceptable salt thereof.

5. The compound according to claim 1 of formula I, said compound being selected from the group consisting of:

1-(3-Allyl-4-oxo-thiazolidin-2-ylidene)-1-amino-3-methyl-imidazolidine-2-thione-4,5-dione;

1-(3-Methylallyl-5,5-dimethyl-4-oxo-thiazolidin-2-ylidene)-1-amino-3-allyl-imidazolidine-2-thione-4,5-dione;

1-(3-Methylallyl-5,5-dimethyl-4-oxo-thiazolidin-2-ylidene)-1-amino-3-methyl-imidazolidine-2-thione-4,5-dione;

1-(3-Methyl-4-oxo-thiazolidin-2-ylidene)-1-amino-3-allyl-imidazolidine-2-thione-4,5-dione:

1-(3-Allyl-4-oxo-thiazolidin-2-ylidene)-1-amino-3-allyl-imidazolidine-2-thione-4,5-dione;

1-(3-Propyl-4-oxo-thiazolidin-2-ylidene)-1-amino-3-methyl-imidazolidine-2-thione-4,5-dione;

1-(3-Propynyl-4-oxo-thiazolidin-2-ylidene)-1-amino-3-methyl-imidazolidine-2-thione-4,5-dione;

1-(3-Allyl-4-oxo-thiazolidin-2-ylidene)-1-amino-3-methyl-5,5-dimethyl-imidazolidine-2-thion-4-one;

1-(3-Allyl-4-oxo-thiazolidin-2-ylidene)-1-amino-3-methyl-imidazolidine-2-thion-5-one;

1-(3-Allyl-5,5-dimethyl-4-oxo-thiazolidin-2-ylidene)-1-amino-3-methyl-imidazolidine-2-thion-5-one;

1-(3-Allyl-4-oxo-thiazolidin-2-ylidene)-1-amino-4-methyl-imidazolidine-2-thion-5-one;

1-(3-Allyl-4-oxo-thiazolidin-2-ylidene)-1-amino-3-methyl-imidazolidine-2-thion-4-one; and 1-(3-Allyl-5,5-dimethyl-4-oxo-thiazolidin-2-ylidene)-1-amino-3-ethyl-imidazolidine-2-thion-4-one;

or a pharmaceutically acceptable salt thereof.

6. A pharmaceutical composition comprising as pharmaceutical active ingredient a compound according to claim 1, in free form or in the form of a pharmaceutically acceptable salt, together with customary pharmaceutical excipients.

7. A method for the therapeutic treatment of rheumatoid diseases, said method comprising the administration of an anti-arthritic effective amount of a compound of claim 1 to an animal in need thereof.

8. A pharmaceutical composition comprising an anti-arthritic effective amount of a compound of claim 1, and a pharmaceutically acceptable carrier.

* * * * *